United States Patent
Mollus et al.

(10) Patent No.: US 7,519,155 B2
(45) Date of Patent: Apr. 14, 2009

(54) DEVICE AND METHOD FOR ADJUSTING IMAGING PARAMETERS OF AN X-RAY APPARATUS

(75) Inventors: Sabine Mollus, Aachen (DE); Jürgen Weese, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 155 days.

(21) Appl. No.: 10/577,098

(22) PCT Filed: Oct. 15, 2004

(86) PCT No.: PCT/IB2004/052111

§ 371 (c)(1),
(2), (4) Date: Apr. 25, 2006

(87) PCT Pub. No.: WO2005/041775

PCT Pub. Date: May 12, 2005

(65) Prior Publication Data

US 2007/0071172 A1  Mar. 29, 2007

(30) Foreign Application Priority Data

Oct. 29, 2003  (EP)  .................................. 03104003

(51) Int. Cl.
H05G 1/44  (2006.01)
G21K 1/12  (2006.01)

(52) U.S. Cl. ........................................ 378/108; 378/16

(58) Field of Classification Search .................. 378/97, 378/98.7, 108, 162, 164, 207, 4.16, 19
See application file for complete search history.

(56) References Cited

U.S. PATENT DOCUMENTS

| | | | |
|---|---|---|---|
| 6,377,656 B1 * | 4/2002 | Ueki et al. | 378/98.7 |
| 6,501,819 B2 * | 12/2002 | Unger et al. | 378/5 |
| 2002/0085672 A1 * | 7/2002 | Ganin et al. | 378/108 |
| 2003/0133534 A1 * | 7/2003 | Bothe et al. | 378/16 |
| 2004/0032928 A1 * | 2/2004 | Toth et al. | 378/108 |

* cited by examiner

Primary Examiner—Irakli Kiknadze

(57) ABSTRACT

The invention relates to a device for adjusting imaging parameters of an X-ray apparatus (1), whereby a user pre-defines on a preliminary image an image region of interest (ROI) and a value of the contrast-to-noise ratio ($CNR_{ref}$) desired for this image region. Based on the current contrast-to-noise ratio ($CNR_m$), new imaging parameters (I, V, L, f, $Q_0$) are then calculated for a generator-control module (7) to control the X-ray apparatus (1) during an image. By means of the method, the X-ray dose may be reduced to a minimum, while at the same time the desired visibility of a region of interest is ensured.

18 Claims, 1 Drawing Sheet

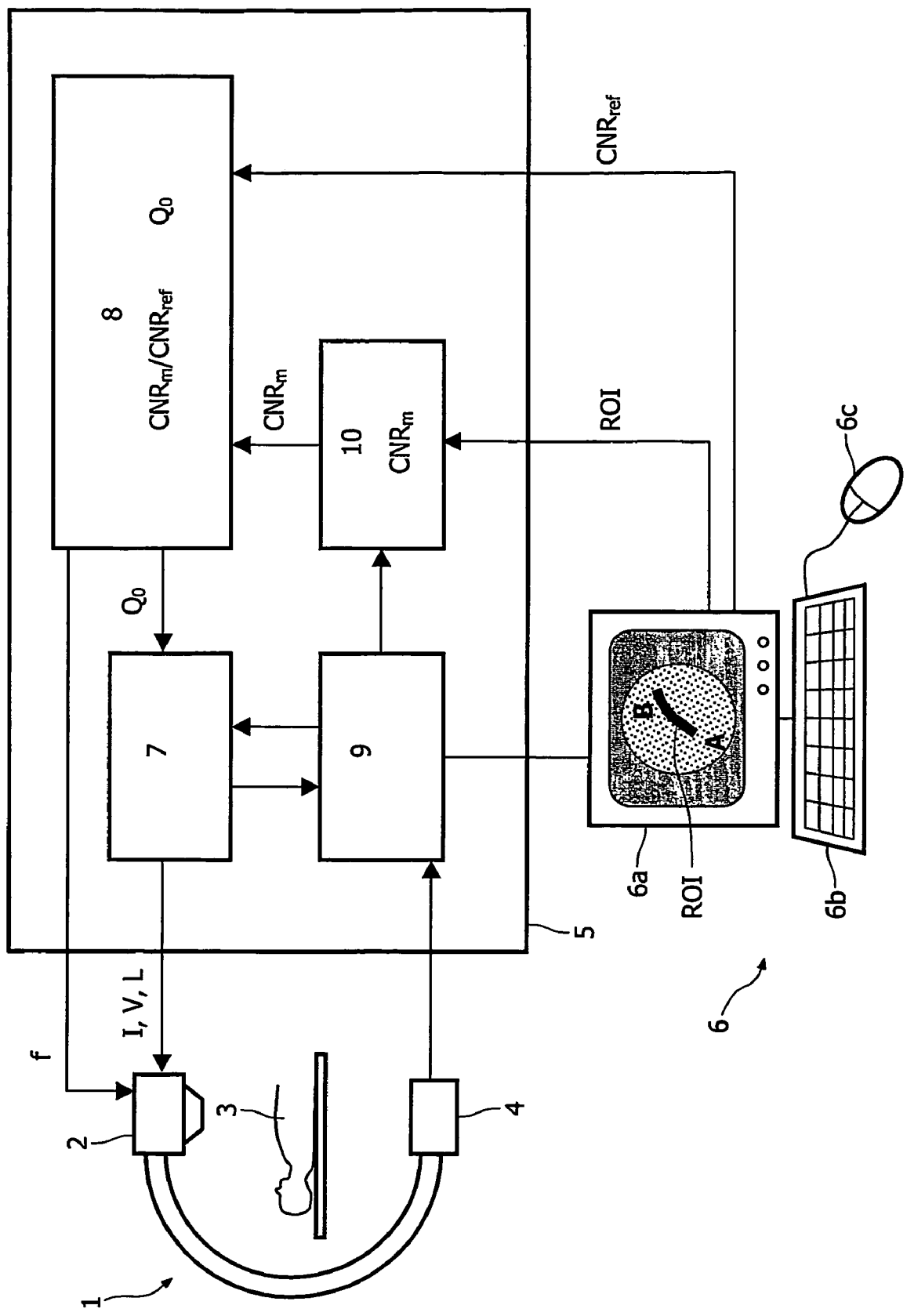

DEVICE AND METHOD FOR ADJUSTING IMAGING PARAMETERS OF AN X-RAY APPARATUS

The invention relates to an adjusting device and method for adjusting imaging parameters, such as in particular the X-ray dose, the tube current, the tube voltage, the pulse length and the filter settings of an X-ray apparatus in order to minimize the radiation load on a patient.

Many diagnostic and therapeutic procedures in medicine are carried out nowadays under X-ray fluoroscopic observation. In order to minimize the radiation exposure of the patient and the personnel, efforts are made to achieve an adequate image quality with the lowest possible radiation doses. With this in mind, manufacturers include in the X-ray equipment APR settings (APR=Anatomical Programmed Radiography), which contain pre-programmed values of the imaging parameters for various imaging scenarios (body regions/organs, clinical considerations, etc.). The values also include parameters of real-time dose control by means of which the dose is substantially controlled such that the mean brightness in a predefined field on the detector or image amplifier (e.g. a circle in the center of the detector) has a predefined value. The user normally has no possibility of better adjusting the APR settings for a particular situation. Such an adjustability would be desirable, however, since the predetermined imaging parameters in particular situations can be sub-optimal, for instance if the absorption model on which they are based is inappropriate under the latest clinical conditions. A typical example of such a situation is a catheter of large diameter used in electrophysiological examinations. A catheter of this type stands out clearly from its background, so that the X-ray images generated using standard parameters typically use a larger X-ray dose than necessary.

In order to adjust imaging parameters of an X-ray apparatus, it is known from JP-11299765 to calculate imaging parameters for a given maximum X-ray dose such that the contrast-to-noise ratio of an interesting object is maximized.

Against this background, it is an object of present invention to provide means for adjusting imaging parameters of an X-ray apparatus which permit minimizing of the radiation load.

This object is achieved by a device with the aspects and features described and discussed via the present disclosure and a method with the aspects and features likewise described and discussed herein, with various advantageous embodiments proviede for illusstrative purposes.

The device according to the invention serves to adjust imaging parameters of an X-ray apparatus and comprises the following components:

A user interface, by means of which, with the aid of a preliminary image generated with the X-ray apparatus, a user may specify an image of interest region such as, for instance, an object (e.g. a vessel section and/or a catheter) and a visibility criterion desired for this image region. Preferably, the visibility criterion is calculated from the selected image region and its surroundings. The user interface typically comprises a monitor for displaying the preliminary images and input means and a keyboard and/or mouse.

A data processing device linked to the user interface and the X-ray apparatus. The data processing device is arranged, for instance with suitable programs, to carry out the following steps:

a) Calculation of adjusted imaging parameters of the X-ray apparatus, during the use of which a predetermined visibility criterion is achieved for the given image region. The given image region and the given visibility criterion for it may particularly be predefined by a user of the device based on a preliminary image, via the user interface.

b) Control of the X-ray apparatus on the basis of the calculated, adjusted imaging parameters.

The device described allows to set imaging parameters of an X-ray apparatus in relation to a concrete application situation, while a desired visibility criterion for an interesting image region such as, for instance, a catheter is taken as a reference. In this way, the user is provided with X-ray images that meet his requirements with regard to visibility of interesting structures, whereby the imaging parameters and therefore the radiation load are automatically set such that the desired result is achieved. By specifying a very low, but simultaneously sufficient, visibility criterion and by limitation to a relevant image region or object, the user may thereby achieve, in particular, that the images are generated with precisely the minimum required dose. This avoids both exposures with a high dose, which generate an unnecessarily high visibility of interesting structures, as well as exposures with too low a dose that would have to be repeated.

The data processing apparatus may, in particular, be arranged for determining the current value of the visibility criterion for a given image region in a preliminary image. A step of this type may be carried out, in particular, within the framework of the calculation of adjusted imaging parameters, so that a current and a desired value of the visibility criterion are available for this. Depending upon the actual definitions chosen for the visibility criterion and the imaging parameters, conclusions concerning the adjusted imaging parameters may often be drawn from the ratio of the two variables.

As imaging parameters of the X-ray apparatus to be adjusted, often those, in particular, come into consideration that influence the X-ray dose per exposure, the intensity of the X-ray radiation during an exposure and/or the quality of the X-ray radiation during an exposure. The X-ray dose is, in general, the fundamental variable on whose stipulation the values of intensity or radiation quality depend. Furthermore, the intensity of the X-ray radiation is typically determined by the tube current of the X-ray source, while the quality of the X-ray radiation is determined by the tube voltage and/or the setting values of filter elements of the X-ray source.

For the definition of visibility criteria which relate to a particular image region or an object and/or the surroundings thereof, there are various possibilities. Preferably, the contrast-to-noise ratio CNR of the interesting image region may be used. This is defined as the quotient of the contrast of the image region to the noise in a predefined relevant region of the image. The "contrast of the image region" may be defined, for instance, as the difference between the (mean) gray value of the image region (or the mean gray value of the edge of the image region) and the (mean) gray value of a (nearer) surrounding area of the image region. Use of a mean gray value suggests itself since in X-ray images, the image background is not homogeneous and may vary greatly. Furthermore, the relevant region of the image in which the noise is determined, preferably extends to the image region and a surrounding area. This takes account of the fact that the image noise in an X-ray image is normally not constant, but varies locally. However, the image noise may possibly also be determined globally and taken as the basis for the whole image. The noise is typically quantified by its associated gray-value range in the relevant region.

The stipulation of an interesting image region may be carried out by the user, in that, for instance, he completely delimits the region of interest with suitable input means or predefines corner points for predefined sectional geometries (rectangular window, etc.). Preferably, however, the data processing device is arranged to support the user in a semi-automatic process in that, by means of at least one pixel predefined via the user interface, it segments an interesting image region on a preliminary image. For instance, the user could stipulate the end points of a catheter section and the data processing device could automatically segment the piece of the catheter lying between these points.

According to further feature of the device, the data processing device is arranged to take account of the influence of image manipulation procedures when calculating adjusted imaging parameters. A typical image manipulation procedure is noise filtration to reduce image noise. If therefore the contrast-to-noise ratio is taken as a basis for the visibility criterion, it is appropriate for the data processing device not to start from the noise values in the original image, but from the noise values after suitable noise filtration.

The device also preferably contains a regulating module for feedback control of imaging parameters of the X-ray apparatus during an X-ray image. The adjusted imaging parameters calculated by the device may represent basic target values, such as the X-ray dose per image, where "dynamic" imaging parameters such as, for instance, the tube current or the tube voltage during an image are subject to constant feedback monitoring. Furthermore, the imaging parameters calculated by the device may also include starting values for feedback-controlled variables. In particular, the control module may contain an image brightness control in order to end the X-ray image when a predetermined threshold for image brightness is achieved.

According to another further feature, the device contains means for detecting changes in the imaging geometry. Changes of this type may, for instance, come about through displacement of the patient table or rotation of the X-ray apparatus. With the imaging geometry, the effect of previously calculated imaging parameters also changes, so that the data processing device is preferably designed such that it adjusts these imaging parameters on detecting a change in the imaging geometry such that the predetermined visibility criterion is (probably) also achieved under the new imaging geometry. For an adjustment of this type, the data processing device may for instance determine the patient's thickness and take it into account.

The invention also concerns a method for adjusting imaging parameters of an X-ray apparatus, including the following steps:
a) Generating of a preliminary image with starting values for the imaging parameters;
b) interactive stipulation of an interesting image region and of a visibility criterion desired for this image region;
c) calculation of adjusted imaging parameters for the X-ray apparatus, with the use of which the predetermined visibility criterion for the predetermined image region is achieved;
d) control of the X-ray apparatus based on the calculated, adjusted imaging parameters.

The method implements, in a general form, the steps executable with a device of the type described above. For a detailed explanation of the details, advantages and further developments of the method, reference is therefore made to the above description.

The invention also concerns an X-ray apparatus having an adjusting device for adjusting imaging parameters, the adjusting device including, for example, a user interface allowing a user to specify an image region of interst and a visibiliy criteria (e.g., a contrast-to-noise ratio of a region of interest) associated therewith, and a data processing device suitable to among other things, calculate adjusted imaging parameters, and control an X-ray apparatus on the basis of such calculated parmeters. Other benefical aspects and features specific to the adjusting device of the present disclosure are discussed hereinafter.

These and other aspects of the invention are apparent from and will be elucidated with reference to the embodiments described hereinafter.

In the drawings, the single FIGURE shows schematically the components of a device according to the invention for adjusting imaging parameters of an X-ray apparatus.

On the left side of the FIGURE, an X-ray apparatus 1 comprising a C-arm with an X-ray source 2 and an X-ray detector 4 are shown. With the aid of the X-ray apparatus 1, 3 X-ray projection images of a patient may be generated, these being passed on to an image recording module 9 in an attached data processing device 5 (workstation). The data processing device 5 also contains a generator-control module 7, which is linked on its output side to the X-ray source 2 in order to control imaging parameters such as, in particular, the X-ray tube current I, the tube voltage V and the pulse length L of the X-ray pulses. The generator-control module 7 is also linked to the image recording module 9 in order, for instance, to carry out feedback image brightness control during an X-ray image. The data processing device 5 is also linked to a user interface 6 which contains a monitor 6a, a keyboard 6b and a mouse 6c. On the monitor 6a, an image generated with the X-ray apparatus 1 may be displayed.

If the user desires a reduction of the X-ray dose and/or an improvement in the image quality, he may activate a suitable adjusting procedure on the data processing device 5. Within the framework of this procedure, firstly a current preliminary image generated with the X-ray apparatus 1 is displayed on the monitor 6a. For the generating of the preliminary image, for instance, a predetermined APR setting is used which was previously selected by the user according to the underlying clinical situation and is set, through a plurality of control parameters, to standard settings. The user is then required to indicate a certain region of interest ROI or an interesting object (an anatomical detail or a certain medical device, such as a catheter) on the image and to stipulate a desired value for a visibility criterion of this region ROI. By means of the interactive intervention by the user, definite identification of a region of interest ROI is, for instance, possible even if the interesting object itself has few characteristics or is ambiguous as, for instance, in the case of a plurality of medical instruments in the visual region with different requirements regarding image quality. The region of interest ROI may naturally also be incoherent or may include a plurality of individual objects, for instance an anatomical object such as the left ventricle and a catheter.

Various possibilities are available for the indexing of an interesting object ROI by the user. For instance, the user may stipulate the start point A and the end point B of an interesting object ROI. The data processing device 5 may then extend the given points A, B to a more detailed object definition using suitable segmentation algorithms.

Furthermore, as previously mentioned, a desired reference value must be stipulated by the user for a visibility criterion of the object. A suitable visibility criterion in this context is the contrast-to-noise ratio CNR, since it places the image noise in relation to the contrast between the object and its background. In particular, the (mean) contrast of the object relative to a surrounding area around the object may be placed in relation to the mean noise in a surrounding area around the object. The user may either stipulate a particular minimum reference value $CNR_{ref}$ for the contrast-to-noise ratio, or a standard value from the system may be used for this, predefined, for instance, in the APR settings.

Given the interesting image region ROI and the reference value $CNR_{ref}$, the data processing device 5 can then determine optimum imaging parameters for the given application, the precise patient and the interesting image region ROI. For this purpose, initially in a module 10 of the data processing device, for the current preliminary image, the contrast between the interesting object ROI and its surroundings is measured and the image noise determined. From these values, the current value $CNR_m$ of the contrast-to-noise ratio can be calculated. In a further module 8 of the data processing device 5, a comparison between the measured contrast-to-noise ratio $CNR_m$ and the desired value $CNR_{ref}$ is subsequently carried out. If the measured value $CNR_m$ is smaller than the desired value $CNR_{ref}$, that is the visibility of the interesting object ROI is too small, the imaging parameters of the X-ray apparatus 1 must be altered such that in the subsequent image recordings, a high X-ray dose is used. If, however, the measured value $CNR_m$ is greater than the reference value $CNR_{ref}$, so that the region of interest ROI is imaged better than required, the X-ray dose can be reduced by a corresponding amount. Typically for carrying out the parameter adjustments described, the ratio between the measured and desired contrast-to-noise ratio, $CNR_m$:$CNR_{ref}$ is calculated. Taking account of technical and legally predefined limit values, the basic specifications for the X-ray images, such as the value $Q_0$ of the desired dose per image may be made available, adjusted dependent upon the calculated ratio and the generator-control module 7. Furthermore, the module 8 may also give commands f to the collimator of the X-ray source 2 in order to control the setting of filter elements.

During the creation of a subsequent X-ray image, dynamic imaging parameters, such as tube current I and tube voltage V are controlled with a brightness-based dose check, whereby the adjusted imaging parameters $Q_0$ are taken into account, in order to depict the interesting object ROI with an optimum X-ray dose.

The X-ray dose Q may generally be influenced by two parameters:
  the radiation intensity, which is determined by the tube current I; and
  the radiation quality, which is determined by the extent of the ray filtration and by the tube voltage.

According to a special embodiment of the method, only the radiation intensity is adjusted, dependent upon the clinical conditions. This means that the number of X-ray photons irradiating the patient is increased linearly in relation to the ratio between the desired and the measured contrast-to-noise ratios $CNR_{ref}$:$CNR_m$.

In another embodiment of the method, it is not only the tube current I, but also the radiation quality that is modulated in order to achieve the desired contrast-to-noise ratio between the interesting object ROI and its surroundings. In the process, various compromises have to be found between different, partially contradictory requirements, in order to find the optimum imaging conditions, e.g.:
  patient thickness vs. image quality (CNR) vs. kVp (peak tube voltage),
  patient thickness vs. patient irradiation vs. kVp.

In order to improve the results obtained with the method, in the calculation of the new dose settings $Q_0$, in module 8 the noise filtration during processing of X-ray images may be taken into account. As the dose is reduced, the noise component of an image signal increases. However, by means of image processing methods, the noise may be partially eliminated and the image quality thereby improved. For this reason, it is advantageous for the exposure parameters to be determined taking account of noise filtration.

The method may be further developed such that the calculated imaging parameters, such as the dose setting $Q_0$, may be adjusted to changes in the acceptance angle and the system geometry. Thus, during the X-ray exposures, the physician may, for instance, displace the patient table or change the position of the C-arm of the X-ray apparatus 1 in order to depict a different perspective of the patient's anatomy. For the handling of such procedures, the patient thickness may be determined from the preliminary image, used to determine the measured contrast-to-noise ratio $CNR_m$. Following changes to the system geometry, the patient thickness and the quotient between the actual contrast-to-noise ratio $CNR_m$ and the desired value $CNR_{ref}$ must then be recalculated to update the dose settings $Q_0$ based on these calculations and to pass them on to the generator-control module 7. In this way, despite an altered geometry, the system can continue to operate at an optimum balance between image quality and radiation dose used.

Summarizing, the above method achieves the following advantages:
  minimizing radiation load while simultaneously ensuring adequate visibility of interesting structures; in that regard, dose reductions by a factor of 2 are possible;
  improvement of visibility of details given inadequate imaging conditions;
  no necessity for segmentation of an interesting object in real time (i.e. no potential source of instability);
  obviousness of the interesting object even in the presence of a plurality of objects in the visual range;
  ensuring a given level of visibility even when the interesting object is situated outside the viewing region;
  robustness with respect to changing the system geometry, since the fundamental visibility model of the object of interest can be extrapolated in relation to various patient thicknesses;
  small changes required to the existing system architectures for integration of the method; in particular the existing brightness-based dosing may remain unchanged;
  the number of APR settings to be implemented may be minimized.

The invention claimed is:

1. An adjusting device for adjusting imaging parameters of an X-ray apparatus, comprising:
  a user interface adapted to, with the aid of a preliminary image, allow a user to specify an image region of interest and a visibility criterion desired for this image region; and
  a data processing device arranged to carry out the following steps:
    a) calculation of adjusted imaging parameters of the X-ray apparatus, by use of which the visibility criterion is achieved for the given image region of interest; and
    b) control of the X-ray apparatus on the basis of the calculated, adjusted imaging parameters,
  wherein the visibility criterion is the contrast-to-noise ratio of the image region of interest.

2. A device as claimed in claim 1, wherein the data processing device is arranged to determine, in a preliminary image, the current value of the visibility criterion for a predetermined image region of interest.

3. A device as claimed in claim 1, wherein the imaging parameters influence the dose per exposure, the intensity and/or the quality of the X-ray radiation generated with the X-ray apparatus.

4. A device as claimed in claim 3, wherein the imaging parameters include the tube current, the tube voltage, the pulse length and/or the setting values of filter elements.

5. A device as claimed in claim 1, wherein, in a preliminary image, on the basis of at least one pixel predefined via the user interface, the data processing device is arranged to segment an image region of interest.

6. A device as claimed in claim 1, wherein the data processing device is arranged to take account of the influence of image processing procedures, in particular noise filtration, when adjusted imaging parameters are calculated.

7. A device as claimed in claim 1, wherein the device includes a control module for feedback control of imaging parameters of the X-ray apparatus during an X-ray image.

8. An adjusting device for adjusting imaging parameters of an X-ray apparatus comprising:
   a user interface adapted to, with the aid of a preliminary image, allow a user to specify an image region of interest and a visibility criterion desired for an image region; and
   a data processing device arranged to carry out the following steps:
      a) calculation of adjusted imaging parameters of the X-ray apparatus, by use of which the predetermined visibility criterion is achieved for the given image region of interest; and
      b) control of the X-ray apparatus on the basis of the calculated, adjusted imaging parameters,
   wherein the device includes a dectector for detecting changes in the imaging geometry and that the data processing device is arranged to adjust the calculated imaging parameters in the case of a change in the imaging geometry such that the predetermined visibility criterion is still achieved, and
   wherein the visibility criterion is a contrast-to-noise ratio of the image region of interest.

9. A device as claimed in claim 8, wherein the data processing device is arranged to determine, in a preliminary image, the current value of the visibility criterion for a predetermined image region of interest.

10. A device as claimed in claim 8, wherein the imaging parameters influence the dose per exposure, the intensity and/or the quality of the X-ray radiation generated with the X-ray apparatus.

11. A device as claimed in claim 10, wherein the imaging parameters include the tube current, the tube voltage, the pulse length and/or the setting values of filter elements.

12. A device as claimed in claim 8, wherein the device includes a control module for feedback control of imaging parameters of the X-ray apparatus during an X-ray image.

13. A device as claimed in claim 8, wherein, in a preliminary image, on the basis of at least one pixel predefined via the user interface, the data processing device is arranged to segment an image region of interest.

14. X-ray apparatus having an adjusting device according to claim 8.

15. A device as claimed in claim 8, wherein the data processing device is arranged to determine, in a preliminary image, the current value of the visibility criterion for a predetermined image region of interest.

16. A device as claimed in claim 8, wherein the imaging parameters influence the dose per exposure, the intensity and/or the quality of the X-ray radiation generated with the X-ray apparatus.

17. A method for adjusting imaging parameters of an X-ray apparatus, comprising the following steps:
   a) generation of a preliminary image with starting values for the imaging parameters;
   b) interactive stipulation of an image region of interest and of a visibility criterion desired for this image region;
   c) calculation of adjusted imaging parameters for the X-ray apparatus, during the use of which the predetermined visibility criterion is achieved for the predetermined image region;
   d) control of the X-ray apparatus based on the calculated, adjusted imaging parameters.

18. X-ray apparatus having an adjusting device according to claim 1.

* * * * *